United States Patent [19]

Scappaticci

[11] Patent Number: 5,011,841
[45] Date of Patent: Apr. 30, 1991

[54] TREATMENT OF DEPRESSION

[75] Inventor: Karen A. Scappaticci, New York, N.Y.

[73] Assignee: Pfizer Inc., New York, N.Y.

[21] Appl. No.: 436,405

[22] Filed: Nov. 14, 1989

[51] Int. Cl.$^5$ .................... A61K 31/50; A61K 31/495
[52] U.S. Cl. ...................... 514/253; 514/255
[58] Field of Search ................. 514/255, 253

[56] References Cited

U.S. PATENT DOCUMENTS 4,507,303  3/1985  Ishizumi et al. .................... 514/255
4,771,053  9/1988  Cott et al. ............................ 514/256

OTHER PUBLICATIONS

The Neuropharmacology of Serotonin–Abstract–No. 100, Wieland, et al., Antidepressant-Like Effects of 5-HT$_{1A}$ Agonists.

Schweizer et al., Psychopharmacology Bulletin, 22, 183–185 (1986).

*Primary Examiner*—Jerome D. Goldberg
*Attorney, Agent, or Firm*—Peter C. Richardson; J. Trevor Lumb; James M. McManus

[57] ABSTRACT

A method for treating depression in humans using a compound of the formula

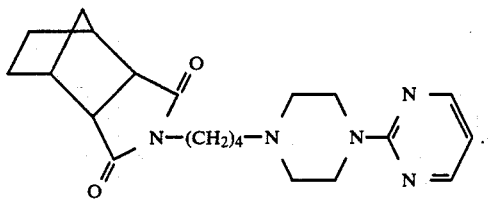

5 Claims, No Drawings

TREATMENT OF DEPRESSION

BACKGROUND OF THE INVENTION

Drugs useful in the treatment of mental depression have generally fallen within one of three categories: (1) blockers of synaptosomal uptake of norepinephrine and serotonin, (2) monoamine oxidase inhibitors and (3) psychomotor stimulants. Antidepressant drugs such as zimelidine, fluoxetine and sertraline appear to act by their ability to selectively block the pre-synaptosomal uptake of serotonin (5-hydroxytryptamine) in the brain. More recently, a group of piperazine structured compounds, including gepirone (U.S. Pat. No. 4,771,053) and buspirone (Psychopharmacology Bulletin, 22, 183 (1986), which are clinically effective anxiolytic agents, are also useful in the treatment of depressive disorders.

SUMMARY OF THE INVENTION

It has now been found that compounds of the structure

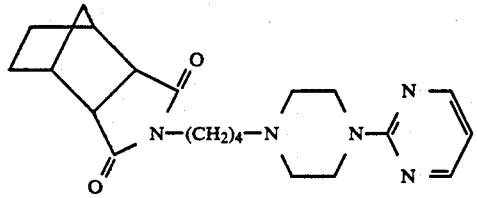

or a pharmaceutically acceptable acid addition salt are useful in the treatment of depressive disorders in human beings.

Preferred is the method wherein the "exo" form of the compound having the formula

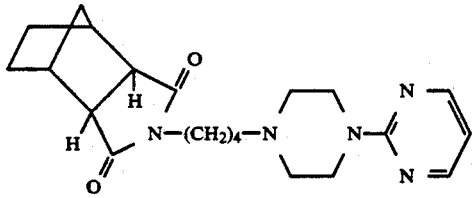

is employed. Especially preferred is the method wherein the depressive disorder is major depression-single or recurrent, bipolar disorder- depressed, depressive disorders not otherwise specified, dysthymia, major depression with or without melancholia or cyclothymia and the daily dose, in unit dosage form, is about 10 mg to about 250 mg. in divided doses administered t.i.d. orally.

The preferred "exo" form is known by the generic name tandospirone. It is also referred to as SM-3997 and is reported along with the "endo" form in U.S. Pat. No. 4,507,303 which is incorporated into the present invention by reference.

As previously mentioned, the compounds of the present method invention are comprised of an "exo" and "endo" form. The "exo" form is of the structure

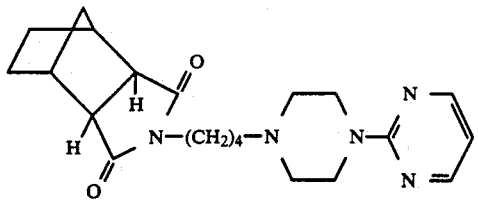

wherein the imide portion of the structure is not under the six membered ring while in the "endo" form of the structure

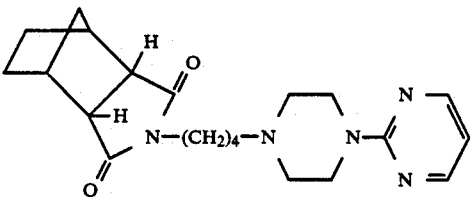

the imide portion is under the six membered ring.

The types of depressive disorders which are especially targetted in the present method invention are fully described and characterized in Diagnostic and Statistical Manual Mental Disorders-Third Revised Edition 1987.

DETAILED DESCRIPTION OF THE INVENTION

Primary depressive illnesses are classified by using standards set forth in the American Psychiatric Association - Diagnostic and Statistical Manual of Mental Disorders (DSM) - Third Revised Edition 1987.

Patients for the study with the compounds of the present method invention were composed of men and women of non-child bearing potential suffering from depression. The study design included a one-week, single-blind placebo baseline period which preceded a six week, double-blind treatment period during which patients received either a placebo or a compound of the present method invention by random allocation. Patients receiving test compounds began at 10 mg t.i.d. (30 mg daily) and were titrated to 40 mg t.i.d. (120 mg daily) over the initial three weeks of double blind treatment.

The performance of the test compounds over placebo was evaluated using the Hamilton depression scale (Ham-D). In this depression-measuring scale the higher the number the more severe the state of depression. An analysis of the study results showed that a significant difference between treatment groups in favor of the test compounds were seen in the Hamilton total score.

When the patients' performance was evaluated by the Global Rating method, an evaluation scale in which a higher score indicates a greater severity of depression, the reductions were significantly greater in the test compound group compared to the placebo group. The two direct measures of improvement, global improvement and therapeutic effect, yielded almost identical results which were significantly in favor of the test compounds.

In summary, it has been demonstrated that the test compounds of the present method invention alleviates major depressive illness, especially major depression with melancholia. These findings have been shown by analysis of changes in standard test results.

The compounds of the present method invention are clinically administered to man via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.14 to about 3.57 mg/kg body weight of the subject per day, preferably about 0.29 to about 2.85 mg/kg body weight per day administered singly or as a divided dose. Smaller or larger doses can be used depending on the drug blood levels achieved by individual patients and on the severity of the depressive disorder. The optimum dosage for the individual subject being treated will be determined by the person responsible for treatment, generally smaller doses being administered initially and thereafter increments made to determine the most suitable dosage. This will vary according to the particular compound employed with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. The injectable solutions prepared in this manner can then be administered intravenously, intraperitoneally, subcutaneously, or intramuscularly.

I claim:

1. A method for treating depressive disorder in a human in need of said treatment which comprises administering to said human an antidepressive effective amount of a compound of the formula

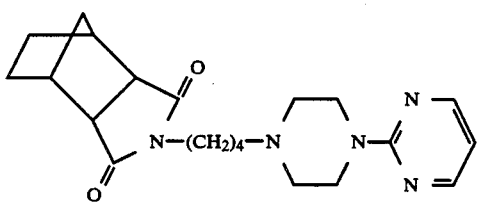

or a pharmaceutically acceptable acid addition salt thereof.

2. The method of claim 1, wherein the compound is the "exo" form of the formula

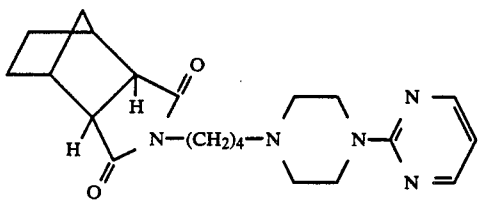

3. The method of claim 2, wherein the depressive disorder is major depression- single or recurrent, depressive disorders not otherwise specified, bipolar disorder- depressed, dysthymia, major depression with or without melancholia or cyclothymia.

4. The method of claim 3, wherein the daily dosage is in unit dosage form from about 10 mg to about 250 mg.

5. The method of claim 4, wherein the daily dosage is divided and administered t.i.d. orally.

* * * * *

REEXAMINATION CERTIFICATE (2379th)

United States Patent [19]

Scappaticci

[11] B1 5,011,841

[45] Certificate Issued Sep. 6, 1994

[54] TREATMENT OF DEPRESSION

[75] Inventor: Karen A. Scappaticci, New York, N.Y.

[73] Assignee: Pfizer Inc., New York, N.Y.

Reexamination Request:
No. 90/003,143, Jul. 26, 1993

Reexamination Certificate for:
Patent No.: 5,011,841
Issued: Apr. 30, 1991
Appl. No.: 436,405
Filed: Nov. 14, 1989

[51] Int. Cl.$^5$ .................. A61K 31/50; A61K 31/495
[52] U.S. Cl. .................................... 514/253; 514/255
[58] Field of Search ............................... 514/253, 255

[56] References Cited

PUBLICATIONS

Peroutka et al., J of Neuropsychiatry and Clinical Neurosciences, vol. 1 No. 3, pp. 254–262, Summer, 1989.
Press et al, Society for Neuroscience Abstract vol. 15, No. 1, p. 225, 1989 abstract No. 94.14, mid Aug. 1989.
Eison, Psychopathology, vol. 22, Suppl. 1, pp. 13–20, 1989 Apr. 14, 1989.
Godbout et al, Society for Neuroscience Abstract vol. 14, No. 1, p. 129 1988 Abst No. 129.1.
Kennett et al, European J. of Pharmacology 138, 53–60, 134, 265–274 (1987).

*Primary Examiner*—Jerome D. Goldberg

[57] ABSTRACT

A method for treating depression in humans using a compound of the formula

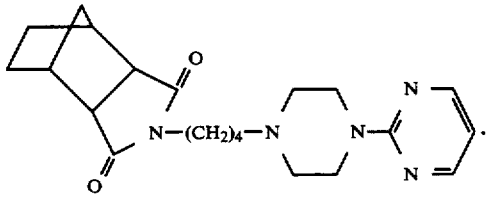

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-5 is confirmed.

* * * * *